United States Patent [19]

Hagen

[11] Patent Number: 4,822,913
[45] Date of Patent: Apr. 18, 1989

[54] PROCESS FOR PREPARING CARBOXYLIC ACIDS FROM ESTERS OF CARBOXYLIC ACIDS

[75] Inventor: Gary P. Hagen, Glen Ellyn, Ill.

[73] Assignee: Amoco Corporation, Chicago, Ill.

[21] Appl. No.: 546,410

[22] Filed: Oct. 28, 1983

[51] Int. Cl.$^4$ .................. C07C 27/02; C07C 51/09; C07C 53/08; C07C 57/04; C07C 57/10; C07C 57/44

[52] U.S. Cl. .................. 562/598; 260/413; 562/400; 562/493; 562/495; 562/496; 562/504; 562/506; 562/601; 562/606; 562/607; 568/877

[58] Field of Search ............... 562/598, 606, 607, 601, 562/495, 496, 504, 506, 400, 493; 260/413, DIG. 33; 568/877; 423/277

[56] References Cited

U.S. PATENT DOCUMENTS 4,269,813 5/1981 Klotz .................. 423/277

OTHER PUBLICATIONS

Namba, S. et al., Chemical Abstracts, 96:34205t 1982.
Klotz, M.R., Chemical Abstracts, 89: 118480x 1978.
Imelik, C. et al., Catalysis By Zeolites, Elsevier Scientific Publishing Co., N.Y., 1980, pp. 60–62.
Raelofsen, D.P. et al., Chemical Abstracts, 79: 118596h (1973).
Banks, A.R. et al., Chemical Abstracts, 88:6294n (1978).

*Primary Examiner*—Vivian Garner
*Attorney, Agent, or Firm*—Reed F. Riley; William H. Magidson; Ralph C. Medhurst

[57] ABSTRACT

Esters of carboxylic acids of the formula RCH$_2$COOR''' and R'CH:C(R'')COOR''' are reacted to form a carboxylic acid and an aliphatic alcohol R'''OH wherein R, R', and R'' are individually selected from the group consisting of —H, alkyl moieties of from 1 to 18 carbon atoms and aralkyl moieties, cycloalkyl moieties and alkylaryl moieties of 3 to 18 carbon atoms and R''' is an alkyl moiety of 1 to 18 carbon atoms in the presence of an AMS-1B borosilicate crystalline molecular sieve catalyst under reaction conditions.

9 Claims, No Drawings

PROCESS FOR PREPARING CARBOXYLIC ACIDS FROM ESTERS OF CARBOXYLIC ACIDS

FIELD OF THE INVENTION

This invention relates to an improved process for preparation of carboxylic acids from carboxylic acid esters of the formula $RCH_2COOR'''$ and $R'CH{:}C(R'')COOR'''$ wherein R, R' and R" are individually selected from the group consisting of —H, alkyl moieties of 1 to 18 carbon atoms, and aralkyl moieties, cycloalkyl moieties and alkylaryl moieties of from 3 to 18 carbon atoms, and wherein R''' is an aliphatic moiety of 1 to 18 carbon atoms, in the presence of a catalyst comprising a borosilicate crystalline molecular sieve. More specifically, methyl acetate is hydrolyzed to acetic acid and methanol. The reaction occurs advantageously at atmospheric pressure in the gas phase at a temperature of from 200° C. to about 450° C. with attendent process advantages over conventional liquid phase routes.

BACKGROUND OF THE INVENTION

It is known to prepare carboxylic acids from carboxylic acid esters at elevated temperatures in liquid or vapor phase in the presence of various catalysts. G.B. Patent No. 1,286,700 teaches the liquid phase hydrolysis of allylic acetate in the presence of water in a molar ratio of 1:1 to 1:10 at a temperature of from 150° to 350° C., under pressure to yield allyl alcohol and acetic acid. Allyl alcohol is removed as it is formed by distilling it overhead. Hydrolysis conditions are selected to minimize the reversible reaction of the allyl alcohol with acetic acid to form the allyl ester. Pressure is at least 5 atmospheres gauge. British Patent No. 1,100,561 teaches the vapor phase hydrochlorolysis of methyl acetate with hydrochloric acid in the presence of a catalyst comprising zinc chloride on kaolin to produce acetic acid and methyl chloride. Methyl chloride is removed as it is formed by distillation. Japanese Kokai No. 78 31,608 (CA89:59664k) teaches gas phase hydrolysis of methyl acetate to acetic acid and methanol in presence of water with $SiO_2$—$Al_2O_3$ catalysts at 150°-300° C.

Other processes are known for preparation of acetic acid compounds from esters of acetic acid. U.S. Pat. No. 1,872,479 teaches a process for producing acetic anhydride from ethylene diacetate by a cracking process in which vapor of ethylene diacetate is suddenly subjected to a high temperature, i.e., between 300° and 450° C., without use of catalysts for a period of 1 to 2 seconds. U.S. Pat. No. 2,730,546 teaches a process for preparing acetic anhydride from methyl acetate in the presence of a mixture of carbon monoxide and hydrogen, N-methyl pyrrolidone and a complex cobalt halide catalyst at a pressure of 200 atmospheres and 180° C. for 15 hours. U.S. Pat. No. 2,789,137 teaches a process for preparing acetic anhydride from methyl acetate in the presence of N-methyl pyrrolidone, cobalt iodide and a mixture of carbon monoxide and hydrogen, at a pressure of 700 atmospheres and a temperature of 190° C. The reaction required 17 hours.

In the oxidation of para-xylene to terephthalic acid, large quantities of acetic acid are used as solvent. Methyl acetate is formed as a by-product of the oxidation and purification process. Quantities of methyl acetate produced by the para-xylene oxidation process are large. A simple gas-phase process which would regenerate acetic acid from methyl acetate and reduce acetic acid losses to a minimum is highly desirable.

An object of this invention is to provide an improved process for preparation of a carboxylic acid from a carboxylic acid ester of the formula $RCH_2COOR'''$ or $R'CH{:}C(R'')COOR'''$ wherein R, R' and R" are individually selected from the group consisting of —H, alkyl moieties of 1 to 18 carbon atoms, and aralkyl moieties, cycloalkyl moieties and alkylaryl moieties of from 3 to 18 carbon atoms, and wherein R''' is an aliphatic moiety of 1 to 18 carbon atoms.

An object of this invention is to provide an improved process for the continuous catalytic hydrolysis of methyl acetate in the vapor phase.

A further object of this invention is to provide an improved process for hydrolysis of methyl propionate in the vapor phase.

These and other objects are achieved by the invention in accordance with which the vapor phase preparation of carboxylic acids from carboxylic acid esters of the formula $RCOOR'''$ and $R'CH{:}C(R'')COOR'''$ wherein R, R', R" and R''' are defined as heretofore, including specifically alpha-, beta-unsaturated carboxylic acid esters, is carried out in the presence of a catalyst comprising a borosilicate crystalline molecular sieve, designated as AMS-1B, having the following composition in terms of mole ratios of oxides:

$$0.9\pm 0.2 M_{2/n}O{:}B_2O_3{:}YSiO_2{:}ZH_2O$$

wherein M is at least one cation, n is the valence of the cation, Y is a value within the range of 4 to about 600, and Z is a value within the range of 0 to about 160, and providing a specific X-ray diffraction pattern.

Esterification and hydrolysis are reversible reactions, depending on reaction conditions. Molecular sieves have been used in the esterification of carboxylic acids. H. R. Harrison, et al., *Chem & Ind*, November 1968, P 1568, teaches use of molecular sieves to selectively adsorb water from a mixture of water and methanol to allow direct isolation of the methyl ester from the esterification reaction by distillation. Sulfuric acid is the catalyst. Heinz, Z.Chem. 1978, 18(1), 22–3 (*Chem.Abst.*, 88, 120584g) teaches the esterification of acetic acid with alcohols using zeolites. Y. T. Eidus, et al., U.S.S.R. Patent 615,060 (*Chem. Abst.*, 89, 108192r) teaches preparation of $C_3$-$C_6$ alkyl esters of $C_3$-$C_7$ carboxylic acids using X- or Y-type zeolites containing Rh, Pd, Co or Ni cations at 240°-250° C. and increased pressure. However, molecular sieves comprising a borosilicate crystalline molecular sieve, designated as AMS-1B, have not been previously taught as catalysts for preparation of carboxylic acids from carboxylic acid esters.

SUMMARY OF THE INVENTION

Disclosed is a process for preparation of carboxylic acids from carboxylic acid esters of the formula $RCH_2COOR'''$ and $R'CH{:}C(R'')COOR'''$ wherein R, R' and R" are individually selected from the group consisting of -H, alkyl moieties of 1 to 18 carbon atoms, and aralkyl moieties, cycloalkyl moieties and alkylaryl moieties of from 3 to 18 carbon atoms, including specifically alpha-beta-unsaturated acid esters, and wherein R''' is an alkyl moiety of 1 to 18 carbon atoms, particularly methyl acetate, in vapor phase at a temperature within the range of 200° C. to about 450° C. at pressures of from 0.5 to 100 atmospheres in the presence of a catalyst comprising a borosilicate molecular sieve, designated as AMS-1B having the following composition in terms of mole ratios of oxides:

$$0.9\pm0.2M_{2/n}O:B_2O_3:YSiO_2:ZH_2O$$

wherein M is at least one cation, n is the valence of the cation, Y is a value within the range of 4 to about 600, and Z is a value within the range of 0 to about 160, and providing a specific X-ray diffraction pattern.

DETAILS OF THE INVENTION

The process of the instant invention relates to a method for preparation of carboxylic acids from carboxylic acid esters of the formula $RCH_2COOR'''$ and $R'CH:C(R'')COOR'''$ wherein R, R' and R'' are individually selected from the group consisting of —H, alkyl moieties of 1 to 18 carbon atoms, and aralkyl moieties, cycloalkyl moieties and alkylaryl moieties of from 3 to 18 carbon atoms and R''' is an alkyl moiety of 1 to 18 carbon atoms, particularly for production of acetic acid from methyl acetate in the presence of AMS-1B borosilicate crystalline molecular sieve catalyst. The process of the instant invention in the presence of water is by a hydrolysis reaction. In the absence of water, the process of the instant invention is by a thermal decomposition reaction. The presence of AMS-1B borosilicate catalyst is essential.

In hydrolysis of methyl acetate, yield is increased over previously taught processes and production of byproducts is minimized. The general method requires the presence of AMS-1B borosilicate crystalline molecular sieve catalyst. The hydrolysis of the carboxylic acid ester is in the gas phase at a temperature within the range of from about 200° C. to about 450° C. at a pressure of from 0.5 to about 100 atmospheres.

The thermal decomposition of the carboxylic acid ester is in the gas phase at a temperature within the range of from about 200° C. to about 450° C. at a pressure of from 0.5 to about 100 atmospheres.

The present invention relates to a process using a synthetic crystalline molecular sieve material, a crystalline borosilicate, as a catalyst. The family of such crystalline borosilicate materials, which are identified as AMS-1B borosilicates, and which are taught in commonly-assigned U.S. Pat. No. 4,269,813, incorporated herein by reference, has a particular X-ray diffraction pattern. Such crystalline borosilicates can generally be characterized, in terms of the mole ratios of oxides, as follows in Equation I:

$$0.9\pm0.2M_{2/n}O:B_2O_3:YSiO_2:ZH_2O$$

wherein M is at least one cation, n is the valence of the cation, Y is between 4 and about 600, and Z representing the water present in such material is between 0 and about 160, or more.

In another instance, the claimed crystalline borosilicate can be represented in terms of mole ratios of oxides for the crystalline material not yet activated or calcined at high temperatures as follows in Equation II:

$$0.9\pm0.2\,[WR_2O+(1-W)M_{2/n}O]:B_2O_3:YSiO_2:ZH_2O$$

wherein R is an alkylammonium cation, M is at least one cation, n is the valence of the cation, Y is a value between 4 and about 600, Z is a value between 0 and about 160, and W is a value greater than 0 and less than 1.

In Equation I, M can represent an alkali-metal cation, an alkaline-earth-metal cation, an ammonium cation, an alkylammonium cation, a hydrogen cation, a catalytically-active-metal cation, or mixtures thereof. In Equation II, M can represent an alkali-metal cation, an alkaline-earth-metal cation, an ammonium cation, a hydrogen cation, a catalytically-active-metal cation, or mixtures thereof.

Advantageously, the value for Y falls within the range of 4 to about 500. Suitably, Y is 4 to about 300; preferably, about 50 to about 160; and more preferably, about 80 to about 120.

Suitably, Z is within the range of 0 to about 40.

The original cation M in the above formulations can be replaced in accordance with techniques well known in the art, at least in part by ion exchange with other cations. Preferred replacing cations include tetraalkylammonium cations, metal ions, ammonium ions, hydrogen ions, and mixtures of the above. Particularly preferred cations are those which render the AMS-1B crystalline borosilicate catalytically active, especially for hydrocarbon conversion. These materials include hydrogen, natural-occurring rare earth metals of Group IIIB, lanthanum, aluminum, metals of Groups IA, i.e., sodium, potassium, lithium, etc.; IIA, i.e., calcium, strontium, barium, etc.; and VIII, i.e., iron, cobalt, nickel, etc. of the Periodic Table of Elements found in the 46th edition of the *Handbook of Chemistry and Physics* published by the Chemical Rubber Company; noble metals, manganese, and other catalytically active materials and metals known to the art. Rare earth metals, lanthanum, sodium and hydrogen are considered especially useful. The catalytically active components, separately or in any combination, can be present anywhere from about 0.05 to about 25 weight percent of the AMS-1B crystalline borosilicate. The form wherein hydrogen replaces the original cation M and n is 1 in the above formulations and is designated HAMS-1B. The hydrogen form of the AMS-1B crystalline borosilicate catalyst imparts an acidic character to the catalyst to improve yields of methyl methacrylate and methyl acrylate. Molecular sieves containing divalent and trivalent cations are generally recognized to impart acidic character to molecular sieves, but the hydrogen ion is considered to impart more acidic character.

Embodiments of such borosilicate compositions useful in the process of the instant invented process provide an X-ray diffraction pattern comprising the following X-ray diffraction lines:

| d (Å) | Assigned Strength |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | wherein the assigned strengths correspond to the following values of relative peak heights:

| Assigned Strength | Relative Peak Height |
|---|---|
| VM | less than 10 |

| Assigned Strength | Relative Peak Height |
|---|---|
| W | 10-19 |
| M | 20-39 |
| MS | 40-70 |
| VS | greater than 70 |

A range of assigned strengths comprises all strengths between the limits shown.

Embodiments of these borosilicates are prepared by the method which comprises: (1) preparing a mixture containing an oxide of silicon, an oxide of boron, a hydroxide of an alkali metal or an alkaline earth metal, an alkylammonium cation or a precursor of an alkylammonium cation, and water; and (2) maintaining said mixture at suitable reaction conditions to effect formation of said borosilicate, said reaction conditions comprising a reaction temperature within the range of about 25° C. to about 300° C., a pressure of at least the vapor pressure of water at the reaction temperature, and a reaction time that is sufficient to effect crystallization. The hydrogen form can be obtained by ion exchange.

The AMS-1B crystalline borosilicate useful in this invention can be in an unsupported form for use either in a fixed bed or fluidized bed reactor. The AMS-1B crystalline borosilicate can be combined with active or inactive materials, synthetic or naturally-occurring zeolites, as well as inorganic or organic materials which would be useful for binding the borosilicate. Well-known materials include silica, silica alumina, alumina, magnesia, titania, zirconia, alumina sols, hydrated aluminas, clays such as bentonite or kaoline, or other binders well known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. Catalytic compositions can contain about 0.1 wt. % to about 100 wt. % crystalline borosilicate material and preferably contain about 10 wt. % to about 80 wt. % of such material and most preferably contain about 30 wt. % to about 65 wt. % of such material.

Catalytic compositions comprising the crystalline borosilicate material of this invention and a suitable matrix material can be formed by adding a finely-divided crystalline borosilicate and a catalytically-active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically-active metal compounds are distributed throughout the matrix material.

Specific details of catalyst preparations are described in U.S. Pat. No. 4,269,813.

It has been found that borosilicate catalysts prepared by the above method are effective in catalyzing the hydrolysis of carboxylic acid esters, particularly methyl acetate, at a temperature within the range of from about 200° C. to about 450° C. and contact time from about 0.1 to about 20 seconds. It has also been found that borosilicate catalysts prepared by the above method are effective in catalyzing the preparation of carboxylic acids from carboxylic acid esters at a temperature within the range of from about 250° C. to about 450° C. either by hydrolysis or ester cleavage in absence of water.

In the hydrolysis reaction of the instant invention, yield of acid as a product is dependent upon the water present as a reactant. Water can be present in a mole ratio of from zero moles of water up to 20:1, moles of water to moles of ester, preferably from 0.2:1 to 2:1, moles of water to moles of ester. Increased presence of water increases the conversion of ester to acid.

The reactant acid ester is of the formula $RCH_2COOR'''$ or $R'CH:C(R'')COOR'''$ wherein R, R', R" and R''' are defined as previously stated. Saturated acid esters can contain alkyl moieties of from 1 to 18 carbon atoms. Examples of saturated acids obtained by the process are acetic acid, propionic acid, n-butyric acid, n-valeric acid, isovaleric acid, n-caproic acid, n-heptanoic acid, capric and lauric acids, phenylacetic acid, gamma-phenylbutyric acid, and 3-methyl-cyclopentylacetic acid. Examples of unsaturated acids which can be obtained are methacrylic acid, crotonic acid, cinnamic acid and sorbic acid.

The reactant esters can be of aliphatic alcohols having from 1 to 18 carbon atoms and 1 to 2 hydroxyl groups. Specific examples of such alcohols include methanol, ethanol, propanol, 2-propanol, butanol, isobutyl alcohol, ethylene glycol, propylene glycol, butanediol, allyl alcohol, etc. to octadecanol.

The catalyst can be used in the form of a fixed bed, a moving bed or a fluidized bed. A fixed bed is preferred.

The instant invented process, as exemplified, is a single-step process for preparation of acetic acid from methyl acetate which is catalyzed effectively by a borosilicate crystalline molecular sieve catalyst as described herein.

The reaction occurs at atmospheric pressure in the gas phase when the reactants are passed through the catalyst in the presence of a nitrogen carrier gas at a temperature of 200° C. to about 450° C., preferably 250° C.–330° C. Above 450° C. significant amounts of known thermal products of methyl acetate are formed, as well as some gaseous by-products. Reactant pressures of from 0.5 to 100 atmospheres can be used. A broad range of reactant ratios may be successfully used for this process.

Liquid hourly space velocity (LHSV) measured in terms of volume of liquid per volume of catalyst per hour ($V_1V_c^{-1}hr^{-1}$), with a constant carrier gas rate, is from about 0.05 to 20.0, preferably from about 0.1 to about 10.0. A LHSV less than about 0.05 results in nonselective decomposition of reactants. A LHSV above 20 results in low conversion of reactants.

The instant invention accordingly comprises a process for hydrolysis or thermal decomposition of carboxylic acid esters of the formula $RCH_2COOR'''$ and $R'CH:C(R'')COOR'''$ wherein R, R' and R" are selected from the class consisting of -H, -alkyl, -aryl, -aralkyl, -cycloalkyl, and -alkylaryl radicals, wherein R''' is an alkyl moiety of 1 to 18 carbon atoms, in the presence of AMS-1B borosilicate crystalline molecular sieve catalyst under reaction conditions at a temperature within the range of from about 200° C. to about 450° C.

The invention will be illustrated by reference to the following specific examples.

EXAMPLE I

The reactor consisted of a quartz tube fitted with a thermocouple through the center of the tube to measure and control temperature. Inlets were provided at the top of the reactor for the carrier gas stream and feed materials. The catalyst bed was positioned in the reactor by an inert support material. Product was removed at the bottom of the quartz tube. Heat was supplied to the reactor by an electric tube furnace.

By use of a syringe pump, methyl acetate (MeOAc) and water were fed into a gas phase reactor containing 1.05 gms of HAMS-1B catalyst (50% by weight on Gamma-alumina) and maintained at a reaction temperature of 300° C. The size (and consequently, the pumping rate) of each syringe was chosen so as to provide a feed containing a 1:1.216 mole ratio of methyl acetate to $H_2O$ (syringe delivery rates were 0.0758 ml/min MeOAc and 0.0207 ml/min $H_2O$). A nitrogen carrier gas flowing through the reactor at a rate of 6 ml/min was maintained, and the catalyst contact time was 2.0 sec. The clear colorless product was collected in a receiver and analyzed by quantitative G.C. analysis and by titration for acetic acid (HOAc). It was found to contain 2.65 gms of HOAc, 0.40 gms of methanol and 5.52 gms of unreacted MeOAc. Conversion of MeOAc was 41.65% with 82.98% selectivity for HOAc. The effluent gas consisted mostly of dimethyl ether.

EXAMPLE II

This example was carried out under similar conditions and with the same reactant ratio as described in Example I except the reaction temperature was maintained at 350° C. and the syringe delivery rates were faster (0.105ml/min MeOAc and 0.0289 ml/min $H_2O$; contact time was 1.35 sec). Conversion of MeOAc was 53.33% with 62.07% selectivity for HOAc.

EXAMPLE III

This example was carried out under identical conditions and with the same reactant ratio as described in Example I except water was excluded as a reactant. (Contact time was 3.84 sec.). Conversion of methyl acetate (MeOAc) was 18.34% with 47.16% selectivity for acetic acid (HOAc). In the absence of water but in the presence of the HAMS-1B catalyst, acetic acid was prepared directly from methyl acetate by an ester cleavage reaction.

What is claimed is:

1. A process for preparation of carboxylic acids from carboxylic acid esters of the formula $RCH_2COOR'''$ and carboxylic acid esters of the formula $R'CH{:}C(R'')COOR'''$ wherein R, R' and R'' are individually selected from the group consisting of -H, alkyl moieties of from 1 to 18 carbon atoms, aralkyl moieties, cycloalkyl moieties and alkylaryl moieties of from 3 to 18 carbon atoms, wherein R''' is an alkyl moiety of 1 to 18 carbon atoms, wherein said process is in the gas phase and comprises a hydrolysis reaction in the presence of water and an ester cleavage reaction in the absence of water, wherein said carboxylic acid esters are passed through an AMS-1B borosilicate crystalline molecular sieve catalyst at a temperature within the range of from about 200° C. to about 450° C. at a pressure of from 0.5 to 100 atmospheres and a liquid hourly space velocity of from about 0.05 to 20, volume of liquid per volume of said catalyst per hour.

2. The process of claim 1 wherein said AMS-1B borosilicate crystalline molecular sieve catalyst is the hydrogen form of AMS-1B.

3. The process of claim 1 wherein the original cation of said AMS-1B borosilicate crystalline molecular sieve catalyst is replaced by a member of the group consisting of rare earth metals, lanthanum, Group IA metals selected from the group consisting of lithium, sodium, potassium, rubidium and cesium and alkaline earth metals selected from the group consisting of magnesium, calcium, strontium and barium.

4. The process of claim 1 wherein said ester of formula $RCH_2COOR'''$ is selected from the group consisting of esters of acetic acid, propionic acid, n-butyric acid, n-valeric acid, isovaleric acid, n-caproic acid, n-heptanoic acid, capric and lauric acids, phenylacetic acid, gamma-phenylbutyric acid and 3-methylcyclopentylacetic acid and R''' is an alkyl moiety of from 1 to 18 carbon atoms.

5. The process of claim 1 wherein said ester of formula $RCH_2COOR'''$ is methyl acetate.

6. The process of claim 1 wherein said acid prepared from said ester of formula $R'CH{:}C(R'')COOR'''$ is selected from the group consisting of methacrylic acid, crotonic acid, cinnamic acid and sorbic acid.

7. The process of claim 1 wherein said acid of ester of formula $R'CH{:}C(R'')COOR'''$ is methacrylic acid.

8. The process of claim 1 wherein water is present as a reactant in a mole ratio of from zero moles of water to 20:1, moles of water to moles of ester.

9. The process of claim 1 wherein liquid hourly space velocity (LHSV) measured in terms of volume of liquid per volume of catalyst per hour ($V_1 V_c^{-1} hr^{-1}$), with a constant carrier gas rate, is from about 0.05 to 20.0.

* * * * *